United States Patent
Konstantino et al.

(10) Patent No.: US 11,033,276 B2
(45) Date of Patent: Jun. 15, 2021

(54) METHODS FOR EMBEDDING AN IMPLANT IN BLOOD VESSELS

(71) Applicant: Sano V Ptd Ltd, Singapore (SG)

(72) Inventors: Eitan Konstantino, Orinda, CA (US);
Michal Konstantino, Orinda, CA (US);
Tanhum Feld, Moshav Merhavya (IL);
Gary Binyamin, Berkeley, CA (US)

(73) Assignee: Sano V Pte Ltd, Singapore (SG)

( * ) Notice: Subject to any disclaimer, the term of this patent is extended or adjusted under 35 U.S.C. 154(b) by 200 days.

(21) Appl. No.: 16/435,172

(22) Filed: Jun. 7, 2019

(65) Prior Publication Data

US 2019/0380716 A1    Dec. 19, 2019

Related U.S. Application Data

(60) Provisional application No. 62/685,008, filed on Jun. 14, 2018.

(51) Int. Cl.
*A61B 17/12* (2006.01)
*A61F 5/41* (2006.01)
*A61F 2/06* (2013.01)

(52) U.S. Cl.
CPC .......... *A61B 17/12109* (2013.01); *A61F 5/41* (2013.01); *A61F 2/06* (2013.01)

(58) Field of Classification Search
CPC ...... A61F 5/41; A61F 2/06; A61B 2017/0649; A61B 2017/00867; A61B 17/1285; A61B 17/1227; A61B 17/12109; A61B 17/068
See application file for complete search history.

(56) References Cited

U.S. PATENT DOCUMENTS

| | | | |
|---|---|---|---|
| 8,240,313 B2 | 8/2012 | Hsu | |
| 10,524,952 B2* | 1/2020 | Konstantino | ........ A61B 17/128 |
| 2002/0029048 A1* | 3/2002 | Miller | .................. A61B 17/064 |
| | | | 606/138 |
| 2005/0277907 A1 | 12/2005 | Jackson | |
| 2009/0248109 A1 | 10/2009 | Forsell | |
| 2011/0007458 A1 | 1/2011 | Liao et al. | |
| 2011/0066254 A1 | 3/2011 | Forsell | |
| 2011/0087337 A1 | 4/2011 | Forsell | |
| 2015/0351912 A1* | 12/2015 | Konstantino | .... A61B 17/12109 |
| | | | 600/38 |
| 2017/0156916 A1 | 6/2017 | Konstantino et al. | |

OTHER PUBLICATIONS

Rao; et al., "Vasculogenic impotence. Arterial and venous surgery. Urol Clin North Am. May 2001;28(2):309-19.".

* cited by examiner

*Primary Examiner* — Jocelin C Tanner
(74) *Attorney, Agent, or Firm* — Wilson Sonsini Goodrich & Rosati

(57) ABSTRACT

Methods and devices are used to treat a dorsal vein to reduce blood flow in patients suffering from erectile dysfunction. For example, a clip may be advanced distally across the deep dorsal vein and an anchor on the clip deployed on a proximal side of the Tunica albuginea. The clip can then be pulled back and a distal anchor on the clip deployed to reduce a cross-sectional area of the deep dorsal vein and anchor the deep dorsal vein to the Tunica albuginea. Anchoring of the dorsal vein to the Tunica albuginea further reduces the cross-sectional area of the deep dorsal vein in response to expansion of the patient's corpora cavernosa.

10 Claims, 8 Drawing Sheets

METHODS FOR EMBEDDING AN IMPLANT IN BLOOD VESSELS

CROSS-REFERENCE

This application claims the benefit of Provisional Application No. 62/685,008, filed on Jun. 14, 2018, the full disclosure of which is incorporated herein by reference.

BACKGROUND OF THE INVENTION

1. Field of the Invention

The present invention relates to systems and methods for treating biological vessels. More particularly, present invention relates to systems and methods for embedding implants in veins to modify the biomechanics of the vein as the vein functions in a surrounding organ. More specifically, the present invention relates to devices and methods for treating erectile dysfunction and for restoring erectile functionality by modifying the veno-occlusive mechanism of vein compression during penile tumescence.

During erection, expansion of the corpora cavernosa (cavernosal volume expansion) causes the occlusion of veins in the penis via a veno-occlusive mechanism primarily in the dorsal veins. The blood volume of the corpora cavernosa is maintained by limiting venous blood outflow due to the veno-occlusive mechanism. The two corpora cavernosa located in the penis fill with blood coming from the deep arteries of the penis causing an erection. Expansion of the corpora cavernosa compresses the associated outflow veins, thus inhibiting the blood outflow and allowing the increased local tissue pressure to maintain an erection.

In a large percentage of men over age 40, this functionality is impaired, commonly referred to as erectile dysfunction (ED). While the cause can be an insufficient inflow of blood (arteriogenic ED), in many cases the cause is the incomplete inhibition of venous outflow (venogenic ED). Incomplete venous occlusion typically results from changes in the biomechanical behavior of the veins that increase resistance to applied tissue pressure. In venogenic erectile dysfunction, the maintenance of the expanded cavernosal volume and tissue pressure is deficient due to incomplete veno-occlusions.

Presently, ED has limited treatment options. Available medications that typically increase blood inflow (such as PDE-5 inhibitors and other vessel dilators) may not be effective in men suffering from venous leak, where blood inflow is not the main problem. Other treatment options usually involve a major surgery and complete occlusion of major vein, but such treatment suffers from poor long-term outcomes and is not recommended by the American Urological Association based on review of data and panel consensus. The failure of complete venous occlusion is believed to be caused by biological changes in the penis, for example, age-associated changes of the connective tissue, including the tunica albuginea and fascial layers, surrounding the penile veins. Those changes limit the effectiveness of the veno-occlusive mechanism. Other changes may include the development of collateral veins, fibrotic tissues and damage to smooth muscle cells.

As an alternative to surgery, various external compression devices have been proposed to treat ED by inhibiting blood outflow. Most such devices, however, require user actuation and are uncomfortable to wear and use.

For these reasons, it would be desirable to provide procedures and devices with improved short-term and/or long-term results for treating ED and restore, reconstruct or enhance fully or partially the veno-occlusive mechanism in related veins. It would further be desirable to provide devices for inhibiting venous flow during the process that leads to erection by correcting or enhancing the veno-occlusive mechanism, such devices may be implanted in relatively simple procedure, with minimal surgical exposure by creating a small incision or no incision at all. In particular, such devices and methods should be simple and effective for treating ED. At least some of these objectives will be met by the inventions described hereafter.

2. Description of the Background Art

Methods and devices for treating ED and for modulating blood flow through veins and arteries are described in US Patent Pubs. 2005/0277907; 2011/0066254; and 2011/007458; and U.S. Pat. No. 8,240,313. See also Rao and Donatucci (2001) Urologic Clinics 28:309-319. Devices for applying external vein compression are described in US2009/0248109 and US2011/0087337.

SUMMARY OF THE INVENTION

The present invention provides methods and devices for embedding blood vessels in the body, particularly veins but also finding use in arteries. The methods rely on placing an implant over, around or through the blood vessel to connect it to adjacent tissue or preferably to a fascial layer, allowing temporary reduction of blood flow when an occlusive mechanism is active. The vessel can also be relocated and be placed through a cut in a fascial layer to further embed the vessel. The term embedding or embedment should be interpreted broadly to mean not only placing the blood vessel into another tissue or organ but also connecting it to adjacent tissue in order to alter the biomechanics and forces applied on such blood vessel during an increase in local tissue pressure or blood inflow to the organ. It also means changing the natural placement of the blood vessel and by that reconfiguring the occlusion response. The implant may be introduced using a delivery device where the implant is carried and subsequently released at the blood vessel.

According to one aspect of the present invention there is provided a device for restoring veno-occlusive response in a vein comprising a device body configured for implantation in, throughout, under or around the vein, the device body being capable of redirecting the vein in such a way that will cause reduction of flow through the vein in response to an increase in tissue pressure around the vein.

According to further features in preferred embodiments of the invention described below, the device body is an open or closed ring configured for implantation around the vein in a manner that will redirect the vein and embed it, at least in one location and preferably in two or more locations along the blood vessel to embed a section of the vein.

According to still further features in the described preferred embodiments, the device body includes an elastically deformable element configured for implantation within or through the vein.

According to still further features in the described preferred embodiments, the element includes two substantially planar arms being capable of anchoring into the tissue underneath or around the vein.

According to still further features in the described preferred embodiments the device includes element capable of penetrating through a fascia or other elastic layer and stay anchored in the tissue underneath the elastic layer. Such device can be external to the vein, for example in a C or U configuration, or pierce through the vein, in both cases to approximate the vein to the fascia layer by being anchored to the layer or through the layer to tissue underneath.

According to still further features in the described preferred embodiments the device embeds the vein in such a way that will limit or block blood flow when local blood pressure increases and nearby tissue filled in blood expands and compresses the vein.

According to still further features in the described preferred embodiments, elements of the device are formed from a Nitinol® wire or elastic metal or elastic polymer or material.

According to still further features in the described preferred embodiments, the vein is a dorsal vein and the adjacent tissue the device connects the vein to is the Tunica albuginea, Superficial' fascia or Buck's fascia and the expandable tissue is penile corpus cavernosa. Ideally the device will be placed between Buck's fascia and the Tunica albuginea and in any case underneath the superficial fascia.

According to still further features in the described preferred embodiments, the increase in tissue pressure results from penile tumescence.

According to another aspect of the present invention, there is provided a system for embedding a vein between two elastic layers to improve veno-occlusion and comprising the device described herein and a delivery device for delivering the device into, through or around the vein such device is made of elastic material or bio-absorbable material or a combination of both.

According to still further features in the described preferred embodiments, the device body is configured with elements capable of anchoring a point or section of a vein to temporarily occlude venous blood flow in response to a force imparted thereupon by the tissue around the device.

According to yet another aspect of the present invention, there is provided a system for embedding vein comprising: (a) one or more clips being size and configured for situating over a region of the vein when positioned there to embed the vein in and restoring veno-occlusion; and (b) a delivery device for penetrating tissue overlying a vein and delivering the clip or clips through one or more walls of the vein.

According to yet another aspect of the present invention, there is provided a system for embedding vein comprising: (a) an implant being size and configured for situating inside a vein to change the location of the vein relative to the surrounding tissue and trigger veno-occlusion in response to increase in local pressure; and (b) a delivery device for penetrating tissue overlying a vein or the vein itself and delivering the implant through one or more walls of the vein.

According to yet another aspect of the present invention, there is provided a system for embedding vein comprising: (a) implant being size and configured for penetrating one or more walls of a vein when positioned there to relocate a section of the vein and embed the vein into tissue or fascial layer and improve veno-occlusion response; and (b) a delivery device for penetrating the vein and delivering the implant through or around one or more walls of the vein into a surrounding fascia layer.

According to still further features in the described preferred embodiments, the implant includes two elements for flanking the vein where the distal element is capable of being anchored in the tissue underneath the vein to or through the Tunica fascia and the proximal element has a lower profile compared to the distal end and resides in proximity to the outer fascia protected by at least the superficial fascia, close to the skin.

According to still further features in the described preferred embodiments, the implant includes two elements where at least one element in made from bio-absorbable material and at least one element is capable of being anchored in the tissue underneath the vein through the fascial layer.

According to still further features in the described preferred embodiments, at least one of the elements includes a tissue piercing end or split-wire, bends, ring or other elements to improve anchoring.

According to still further features in the described preferred embodiments, the clip or the implant includes two curved regions linked via a linear strut.

According to still further features in the described preferred embodiments, the implant is fabricated from a shape memory material capable of assuming a tissue compressive shape following delivery.

According to still further features in the described preferred embodiments, the implant assumes a substantially linear configuration when disposed in the delivery device. A substantially linear configuration means that clip will occupy a small diameter to facilitate delivery while it may increase in length.

According to still further features in the described preferred embodiments, the clip is configured for embedding the vein to or into the Tunica albuginea to improve veno-occlusion.

According to yet another aspect of the present invention, there is provided a method of controlling blood flow through a vein comprising: (a) delivering an implantable clip having one or more elements, where at least one elements is capable of anchoring the vein into the Tunica albuginea and (b) releasing the clip from the delivery system to embed a region of the vein and improve the veno-occlusive response of the vein; wherein the implant resides underneath the superficial fascia.

In one particular aspect, the present invention provides a method for constricting blood flow through a dorsal vein. The dorsal vein overlies a Tunica albuginea (TA), and the method comprises providing an implantable clip having a distal anchor and a proximal anchor. The distal anchor is penetrated in a distal direction through opposed walls of the dorsal vein and further through at least the TA. After penetrating the TA, the distal anchor is deployed on a distal side of the TA and the proximal anchor is deployed on a proximal side of the dorsal vein. Deployment of the distal anchor on the distal side of the TA couples the dorsal vein to the TA in a manner that immobilizes the vein relative to the TA. The distal anchor and the proximal anchor may be spaced-apart along an axial length of the clip so that, once deployed, the anchors will constrain and at least partially collapse the opposed walls of the dorsal vein to reduce the cross-sectional area thereof. In addition to the initial reduction of luminal area, such reshaping of the dorsal vein promotes further closure of the dorsal vein lumen in response to external pressure applied as the corpora cavernosa expand during arousal. That is, "kinking" the walls of the dorsal vein provides an initiation site for further closure in response to the external pressure applied by the corpora cavernosa, and such kinking is promoted by coupling of the clip to the underlying TA. In particular, anchoring of the dorsal vein to the TA immobilizes the dorsal vein so that expansion of the corpora cavernosa will act more directly on the vein to cause the reduction in cross-sectional area.

In further specific aspects of the methods herein, the clip may comprise an elongate wire body having an axial length and a preformed coil at each end, i.e. the distal anchor and the proximal anchor, respectively. The distal anchor will be configured deploy against a distal surface of the TA, while the proximal anchor will typically be deploys against a proximal surface of the dorsal vein, although in some instances, the proximal coil may be configured to deploy against a proximal surface of the Buck's fascia or the superficial fascia.

In other specific instances, the penetrating step may comprise advancing a needle in a distal direction through the opposed walls of the dorsal vein and the TA optionally through the Buck's fascia and/or the superficial fascia. Access through the Buck's fascia and/or the superficial fascia may alternatively be established by a surgical incision followed by needle penetration through the dorsal vein and the TA. The needle carries the clip, and will be advanced sufficiently through the TA to dispose the distal anchor on a distal side of the TA. The distal anchor is typically released and expanded after the distal anchor reaches the distal side of the TA. The needle may then be drawn proximally in order to position the proximal anchor over the proximal side of the dorsal vein. The proximal anchor may then be released to expand from the needle and seat on the proximal surface of the dorsal vein to complete compression of the dorsal vein and anchoring of the dorsal vein to the TA. In other instances, however, the needle might be further proximally retracted to position the proximal anchor over the Buck's fascia or the superficial fascia prior to deployment of the proximal anchor.

In preferred instances of the present invention, the dorsal vein is the deep dorsal vein.

The present invention successfully addresses the shortcomings of the presently known configurations by providing devices for treating erectile dysfunction that can be implanted using minimally invasive surgery and do not require manual activation or implanted actuators for operability.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention is of a device which can be used to treat erectile dysfunction. Specifically, the present invention can be used to embed any of the penile veins, such as the dorsal vein, and trigger veno-occlusive response during penile tumescence thereby enabling an individual to achieve and maintain a full erection.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 1A:
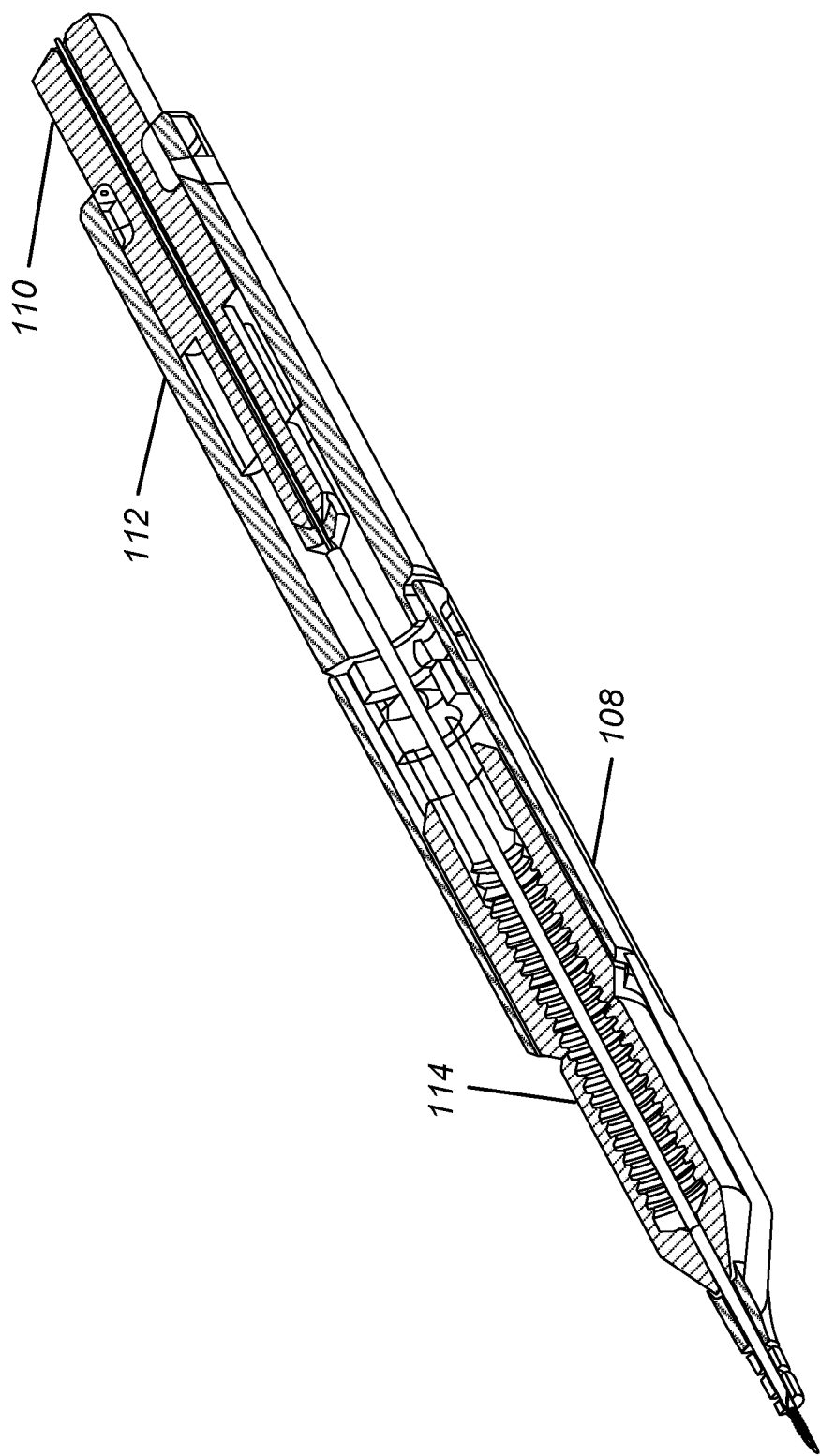
FIGS. 1A-1C illustrate a compression implant delivery apparatus useful in performing the methods of the present invention the present invention.
Figure 1B:
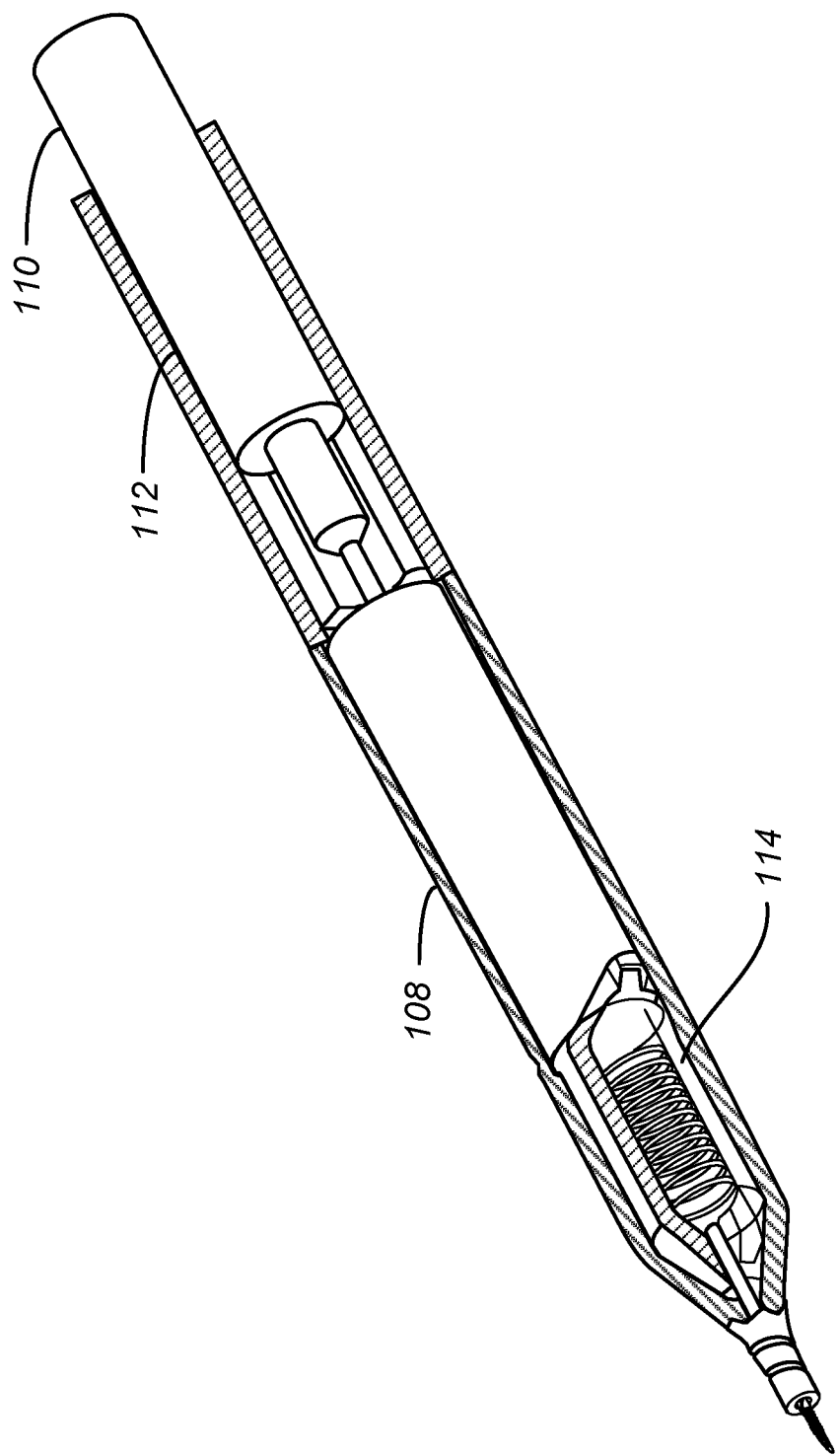
Figure 1C:
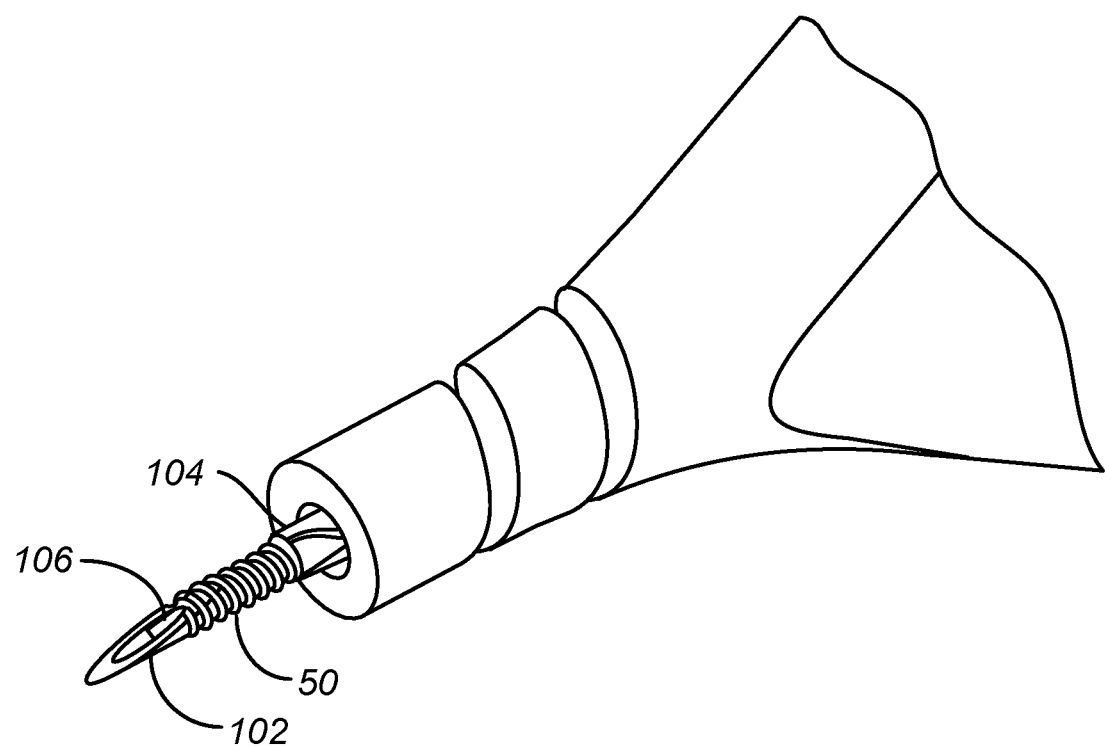

As shown in FIGS. 1A-1C, an apparatus 100 useful for implanting a vein-occluding implant illustrated here as a self-deploying coil 50 which is initially tightly wrapped over a needle cannula 102 (FIG. 1C). Cannula 102 typically has a diameter of about 0.5 mm. Coil 50 typically has a length when stretched out of about 3 mm-4 mm length thus having about 6 to 8 turns when constrained over the cannula 102 Apparatus 100 further includes an over tube 104 holding the proximal end of coil 50 and an inner tube 106 holding the distal end of coil 50.

Cannula 102 has a self-penetrating tip similar to a hypodermic needle and can be inserted through the penile tissue and opposed vein walls to position coil 50 through the vein. At this depth the distal end of housing 108 of apparatus 100 compresses the vein flat. Blood flowing out at the top of inner tube 106 serves as an indication for correct depth. The distal end of coil 50 is then released by pressing knob 110 thereby moving inner tube 106 distally and unlocking the distal end of coil 50. The distal 1-1.5 coils of coil 50 are then threaded by holding the housing 108 while rotating knob 112 about 3 turns. At the end of this step the distal 1-1.5 coils are anchored underneath the vein. The number of rotations is limited by a counter 114 that can move up knob 112 three times the thread lead angle. Outer tube 104 is then rotated about one third of a turn using knob 114 of outer tube 104 to release the proximal end of coil 50.

Apparatus 100 and other suitable clip and coil introducers are described in more detail in commonly owned U.S. Patent Publ. No. 2017/0156916, the full disclosure of which is incorporated herein by reference.

A particular device suitable for embedding in a 3 mm vein can have a circular ring, semi-ring or bend or anchor of 1.5 mm or between 0.5 to 3 mm/non-constrained length of 2.5 mm. This device can be straightened to a linear wire, constrained and stored, pre-loaded, in a small gauge needle. When straightened the length of the device can be 5-10 mm depending on non-constrained shape of the device (spiral, S-shaped etc). The distal end of the device can be released into or through a fascial layer, embedding an anchor point further away from the delivery apparatus. As the delivery apparatus retracts the proximal end of the device will be released out of the vein, forming a predetermined shape and allowing for the vein to be embedded. In this case only the central device portion is released inside the vessel, with minimal footprint exposed to blood flow.

As is further described herein, embodiments of the present device are configured to embed the vein to the tunica albuginea and restore the veno-occlusive response of the vein when the pressure surrounding the vein increases as is the case with tumescence. Thus, according to one aspect of the present invention there is provided a device for treating erectile dysfunction. As used herein, the phrase "erectile dysfunction" refers to an inability or limited ability to achieve and/or sustain an erection suitable for sexual intercourse One aspect of the present device includes a device body which is configured for implantation in, through or around a vein, such as the penile dorsal vein, which drains the penile corpus cavernosa, in a way that embeds the vein to a fascial layer, such as the Tunica albuginea, for the treatment of erectile dysfunction by restoring the veno-occlusive pressure response of the vein.

Penile erection is triggered by the parasympathetic division of the autonomic nervous system (ANS), causing nitric oxide (a vasodilator) levels to rise in the trabecular arteries and smooth muscle of the penis. The arteries dilate causing the corpora cavernosa of the penis (and to a lesser extent the corpora spongiosum) to fill with blood increasing the hydrostatic pressure applied by these tissues to veins running therethrough. Tumescence is maintained by the ischiocavernosus and bulbospongiosus muscles which compress some of the veins of the penis restricting the egress and circulation of this blood.

In venogenic erectile dysfunction, the corpus cavernosa (and to a lesser extent the corpus spongiosum) are engorged with blood, however, failure to prevent egress of blood through the veins leads to loss of tumescence.

The present invention embeds or relocates the vein in a way that increases the external forces applied to the vein the by the tissues surrounding it to temporarily block or reduce outflow of blood through the veins.

To enable such functionality, the present device may include any or all of the following features:
(i) the device may be sized and configured for implantation in, through or around one or more veins or vein segments;
(ii) the device can be anchored to a fascial layer or through a fascial layer
(iii) the device may comprise segments, such as arms, struts, bars, flanges, pads, or the like, that relocate the vein to a position in which the vein can completely or partially collapse temporarily during erection; and
(iv) the device may be deliverable via a minimally invasive procedure.

Several configurations of the present device are envisaged herein. A device for implantation around the vein can be configured as an open ring, semicircular or bended clip for embedding a vein segment.

A device for implantation through the vein can include coils or clips which can hold the vein in an embedded to the Tunica albuginea in a relocated position. In a preferred embodiment the method consists of an implantable device and delivery system to approximate the deep dorsal vein to the Tunica Albuginea by anchoring in the Tunica Albuginea fascia (or piercing through this fascia layer) and residing underneath the superficial fascia layer and ideally underneath the Buck's fascia layer. Such configuration may minimize discomfort and may reduce the risk of migration or dislodgement. The implant is therefore placed between at least one internal and one external fascia layers while compressing, piercing or embedding the deep dorsal vein. The same method can be applied to other penial veins. The present device can be fabricated from any material including polymers, bioabsorbable or biodegradable polymers and alloys. The present device can be fabricated from shape memory materials to facilitate implantation through, for example, a hand-held applicator. In such cases, the device can be linearized or stored for delivery, and once released from the applicator it assumes an active shape.

Figure 2A:
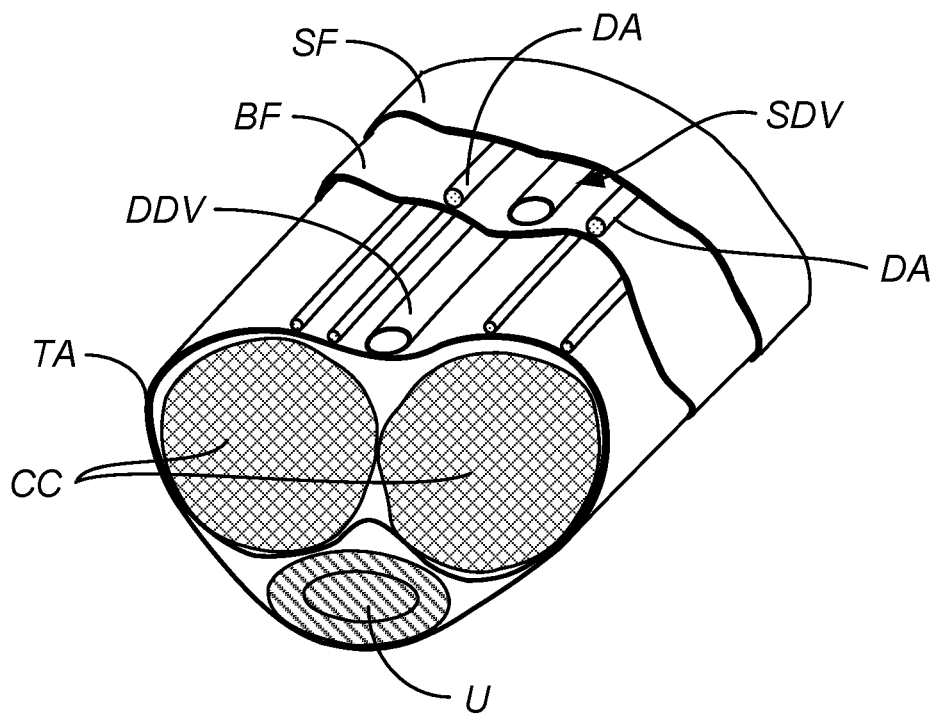
FIGS. 2A and 2B are schematic illustrations of the anatomy of a penis
Figure 2B:
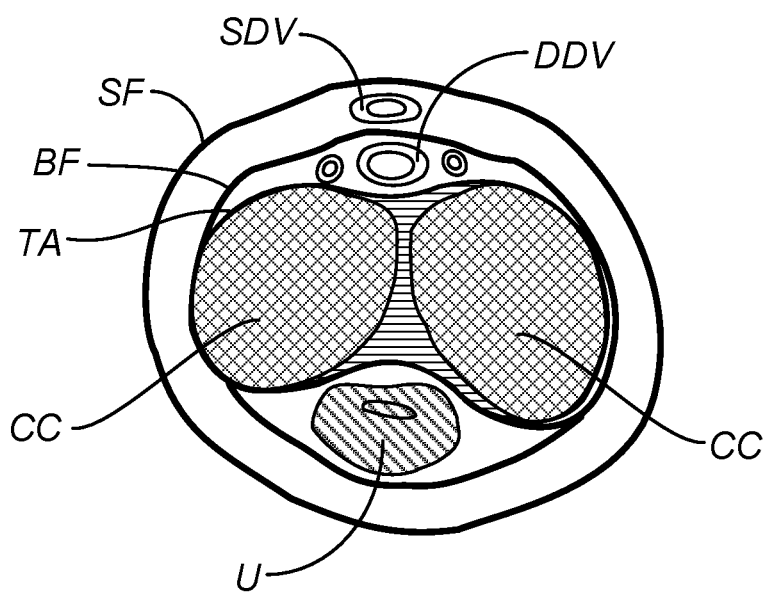

FIGS. 2A and 2B are a schematic illustrations of the human penis anatomy showing the superficial fascia SF, Buck's fascia BF, the Tunica albuginea TA, the deep dorsal vein DDV the superficial dorsal vein SDV, the corpora cavernosa CC, the dorsal arteries, and the urethra U.

Figure 3A:
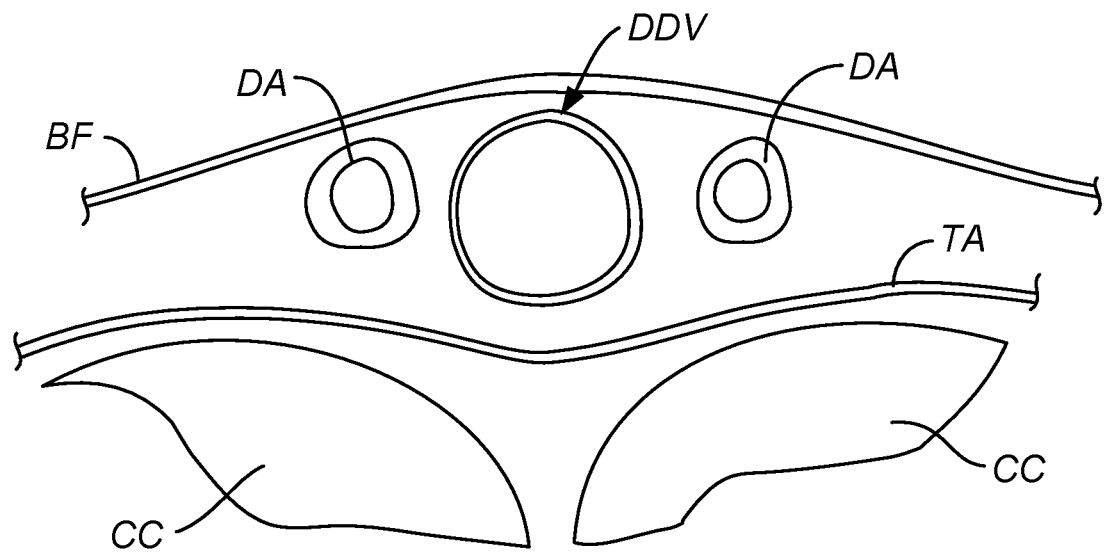
FIGS. 3A-3D illustrate a clip implantation protocol in accordance with the principles of the present invention.

Referring now to FIGS. 3A-3D, implantation of an exemplary coil implant 306 in accordance with the principles of the present invention will be described. FIG. 3A is an enlarged view of the anatomy shown in FIGS. 2A and 2B, with detail of the region between the Buck's fascia BF and the Tunica albuginea TA. In particular, the location of the deep dorsal vein DDV and the two deep arteries DA are shown.

Figure 3B:
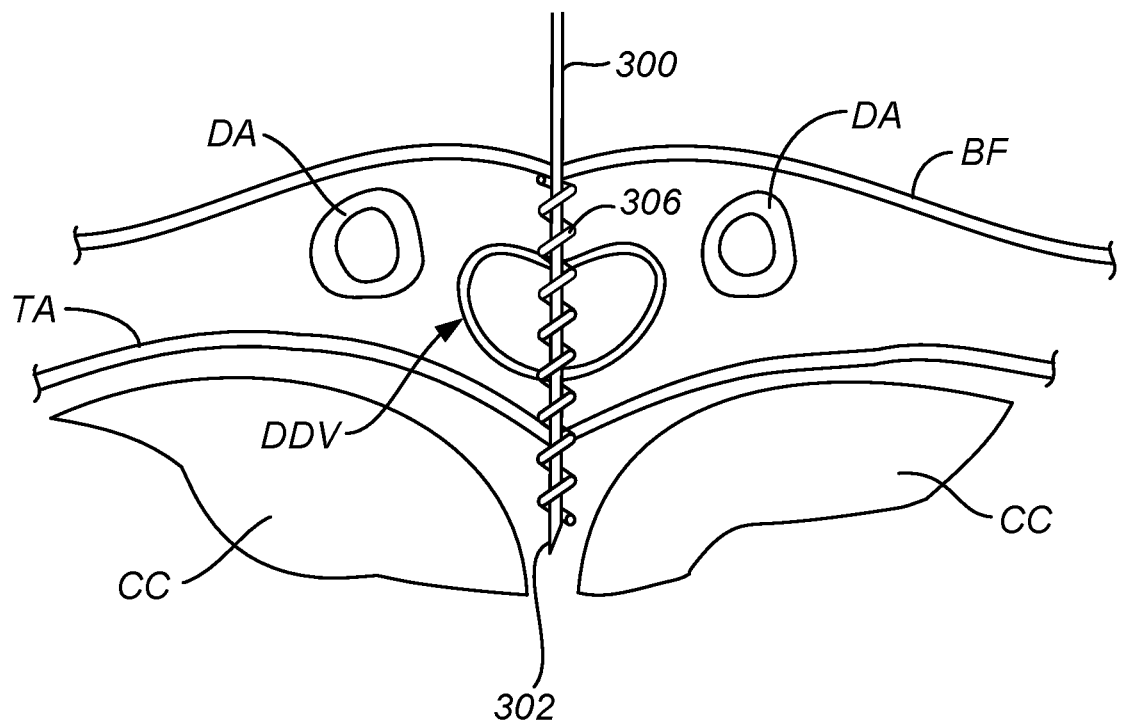

As further shown in FIG. 3B, a needle 300 having a self-penetrating tip 302 which carries the coil implant (clip) 306 may be advanced through the Buck's fascia BF, through the opposed walls of the deep dorsal vein DDV, and finally through the Tunica albuginea TA.

Figure 3C:
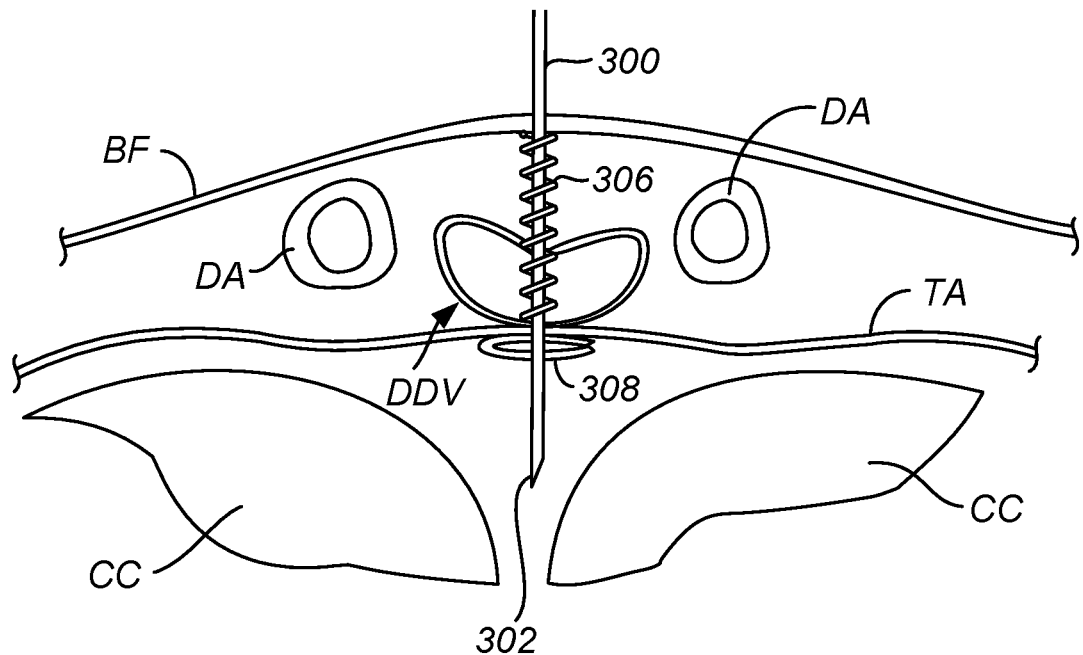

As next shown in FIG. 3C, a distal anchor 308, typically in the form of a distal coil, is released from the needle 300 and engages a proximal surface of the Tunica albuginea TA. The needle may then be drawn proximally to firmly seat the distal coil 308 against the distal surface of the Tunica albuginea TA, resulting in partial collapse of the deep dorsal vein DDV, as shown in FIG. 3C.

Figure 3D:
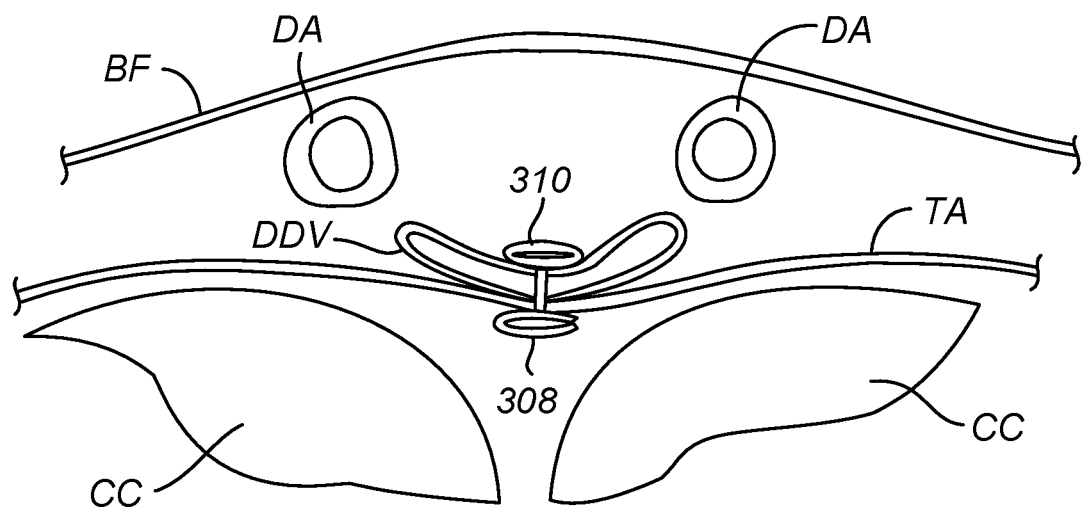

As further shown in FIG. 3D, after the needle 300 has been proximally retracted, a proximal coil 310 may be released from the needle in order to seat against a proximal surface of an opposed wall of the deep dorsal vein DDV to further collapse the deep dorsal vein and to complete anchoring of the deep dorsal vein to the Tunica albuginea TA. The degree to which the deep dorsal vein DDV is collapsed will depend on the structure and dimensions of the coil implant (clip) 306.

Figure 5A:
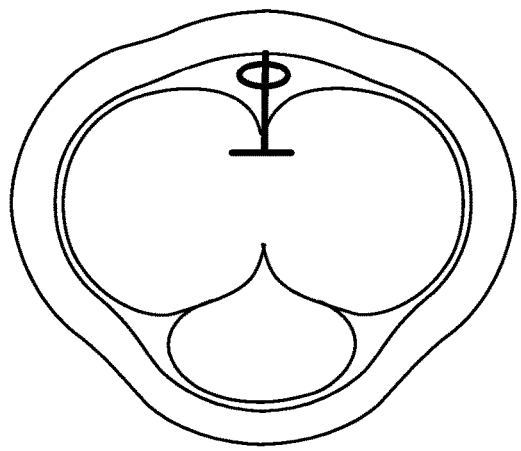
FIGS. 5A-5C illustrates the different configurations of an implant device suitable for use in the methods of the present invention.
Figure 5B:
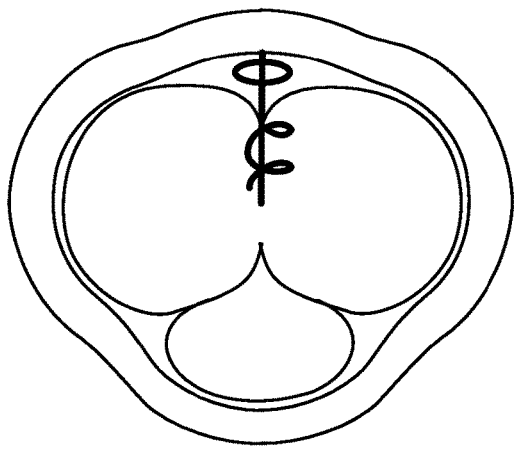
Figure 5C:
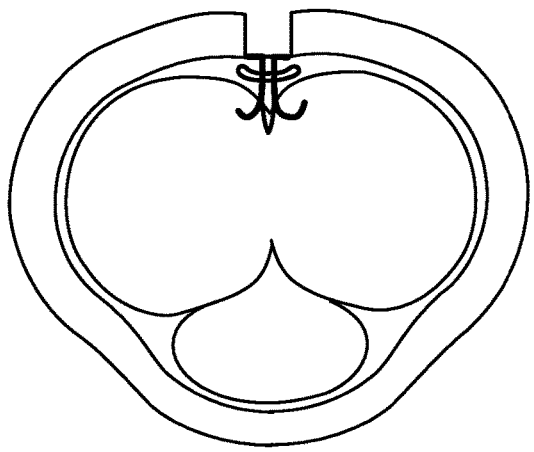

A number of specific anchor designs are shown in FIGS. 5A through 5C, as discussed in more detail below.

Figure 4:
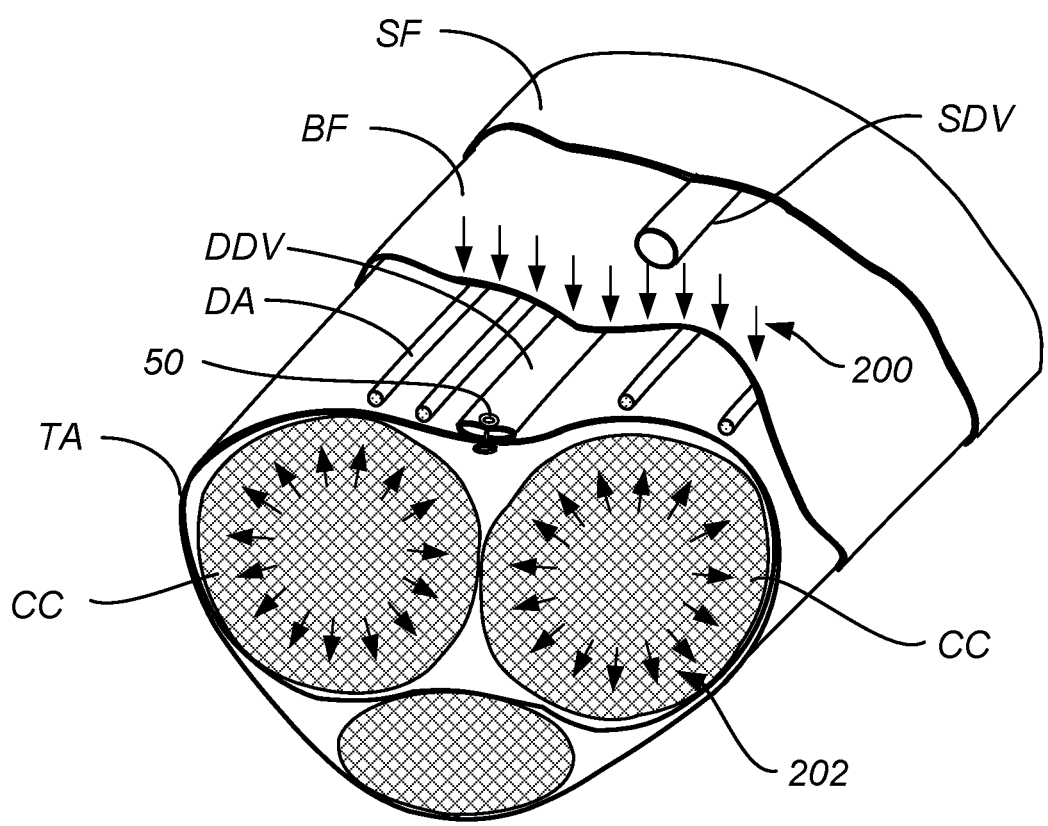
FIG. 4 illustrates an exemplary vein occlusion effected by surrounding tissue in response to increase in tissue volume.

FIG. 4 illustrates an "embedded" vein after implantation of the clip 50. While constriction of the deep dorsal vein DDV is illustrated, other veins can be embedded as well and anchored by the implant to the underlying tunica albuginea. Compared to the rest of the vein, the embedded section of the deep dorsal vein DDV sits deeper into the surrounding tissue and is locked into the fascial layer (tunica albuginea) so the can be affected by changes to tissue blood pressure and swelling of surrounding tissue.

FIG. 4 further illustrates the restored veno-occlusive mechanism of the embedded vein. Similar to healthy men, during penile erection the corpora cavernosa CC of the penis and to a lesser extent the corpora spongiosum fill with blood and expand, thereby increasing the hydrostatic pressure applied by these tissues to the embedded vein. Tumescence is maintained by the activation of venous occlusion. A preferred location for the implant in this method is in proximity to the deep dorsal vein in the space beneath (or through) Buck's Fascia BF and extending through the tunica albuginea TA, Once sexual arousal subsides, the arteries feeding the tissue (corpus cavernosa) constrict and tumescence decreases, thereby decreasing pressure on the vein and allowing blood outflow. The forces applied by the expanding corpora cavernosa CC and the Bucks' fascia BF to the deep dorsal vein DDV now embedded closer to the cavernosa and subject to more compression forces are indicated by the arrows 200 and 202, respectively.

FIGS. 5A-5C illustrates the different configurations of the device. The implant can be fabricated from a shape memory material (e.g. Nitinol®) and can be easily delivered through a needle to self-assume its active shape following delivery once unconstrained. It can also be made of polymer or metal, either elastic or super-elastic. It can be inserted and placed around the dorsal vein via a small incision in the penile skin and fascia.

In one configuration the implant is typically made of a wire with its distal anchor in the shape of disk (FIG. 5A) a coil (FIG. 5B) or split fork (FIG. 5C), and is configured to be inserted through the blood vessel and deployed with one or more coils underneath the blood vessel. The distal anchor is typically made of an elastic alloy, preferably Nitinol®, alternatively being formed from a stainless steel, cobalt or other alloy. The coil wire is usually round but alternatively could have a square, triangular or other cross-sectional profile. The proximal anchors may be configured the same or differently that the distal anchor.

Embedding of the vein facilitates further vessel collapse under external pressure from the surrounding tissues during tumescence by positioning it closer to the fascia and to the expanding tissues of the cavernosa. Thus, while the initial embedding of the vein caused by implantation of the device does not necessarily reduce blood flow through the vein, the rise in external forces of tissues during tumescence in the new location of the vein further collapses the vein and further decreases or completely blocks blood flow therethrough.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of constricting blood flow through a dorsal vein overlying a Tunica albuginea, said method comprising:
 (a) providing a clip having a distal anchor and a proximal anchor;
 (b) penetrating the distal anchor in a distal direction through opposed walls of the dorsal vein and further through the Tunica albuginea;
 (c) deploying the distal anchor on a distal side of the Tunica albuginea; and
 (d) deploying the proximal anchor on a proximal side of the dorsal vein;
 wherein a cross-sectional area of the dorsal vein is reduced and the dorsal vein is anchored to the Tunica albuginea.

2. The method of claim 1, wherein anchoring of the dorsal vein to the Tunica albuginea further reduces the cross-sectional area of the dorsal vein in response to expansion of a corpora cavernosa.

3. The method of claim 1, wherein the clip comprises an elongate wire body having preformed coils at each end forming the distal anchor and the proximal anchor.

4. The method of claim 1, wherein the distal anchor deploys against a distal surface of the Tunica albuginea.

5. The method of claim 1, wherein the proximal anchor deploys against a proximal surface of the dorsal vein.

6. The method of claim 1, wherein penetrating comprises advancing a needle carrying the clip in a distal direction through opposed walls of the dorsal vein and further through the Tunica albuginea.

7. The method of claim 6, wherein the distal anchor is released and expands from the needle after said distal anchor reaches the distal side of the Tunica albuginea.

8. The method of claim 7, further comprising drawing the needle proximally back to position the proximal anchor on the proximal side of the dorsal vein.

9. The method of claim 8, wherein the proximal anchor is released and expands from the needle after said proximal anchor is positioned on the proximal side of the dorsal vein.

10. The method of claim 1, wherein the dorsal vein is a deep dorsal vein.

\* \* \* \* \*